US008062679B2

(12) United States Patent
Clement et al.

(10) Patent No.: US 8,062,679 B2
(45) Date of Patent: Nov. 22, 2011

(54) COMPOSITION FOR MAINTAINING ANDROGEN AND ANDROGEN-LIKE UPTAKE POTENTIAL BY CELLS

(75) Inventors: Ken Clement, Mississauga (CA); Shan Chaudhuri, Mississauga (CA); Michele Molino, Mississauga (CA); Phil Apong, Mississauga (CA)

(73) Assignee: Northern Innovations and Formulations Corp., Oakdale (CA)

( * ) Notice: Subject to any disclaimer, the term of this patent is extended or adjusted under 35 U.S.C. 154(b) by 108 days.

(21) Appl. No.: 11/746,825

(22) Filed: May 10, 2007

(65) Prior Publication Data

US 2008/0279837 A1    Nov. 13, 2008

(51) Int. Cl.
*A61K 36/00* (2006.01)
*A61K 31/4045* (2006.01)
*C07D 313/00* (2006.01)

(52) U.S. Cl. .................... 424/725; 514/415; 549/409

(58) Field of Classification Search .................. None
See application file for complete search history.

(56) References Cited

U.S. PATENT DOCUMENTS

| 5,804,596 | A  |   | 9/1998  | Majeed et al.     |         |
|-----------|-----|---|---------|-------------------|---------|
| 2004/0005368 | A1 | * | 1/2004  | Mann et al. ......... | 424/725 |
| 2005/0095233 | A1 |   | 5/2005  | McCleary et al.   |         |
| 2005/0238654 | A1 | * | 10/2005 | Takeda ............ | 424/195.15 |
| 2006/0051435 | A1 | * | 3/2006  | Udell et al. ...... | 424/725 |

FOREIGN PATENT DOCUMENTS

WO          9702041 A1    1/1997

OTHER PUBLICATIONS

Prunet-Marcassus et al. Melatonin Reduces Body Weight Gain in Sprague Dawley Rats With Diet Induced Obesity. Endocrinology. 144 (12): 5347-5352.*
Idebenone. Alternative Medicine Review. vol. 6, No. 1. 2001. pp. 83-36.*
Armstrong et al. The Coenzyme Q 10 Analog Decylubiquinone Inhibits the Redox-Activated Mitochondrial Permeability Transition. The Journal of Biological Chemistry. vol. 278, No. 49 Dec. 5, 2003. pp. 49079-49084.*
Hu et al. Hepatoprotective Effet of Ginsenoside RB1 and Compound K on Tert-Butyl Hydroperoxide-Induced Liver Injury. Liver International. 25. 2005. 1069-1073.*
Wu et al. Quality Evaluation of the Commercial Ginsengs by High-Performance Liquid Chromatography. Yixue Yanjiu (1993), 14, (1). English Abstract.*
Kraemer WJ, et al. Androgenic responses to resistance exercise: effects of feeding and L-carnitine. Med Sci Sports Exerc. Jul. 2006;38(7):1288-96.
Inoue K, et al. Androgen receptor antagonist suppresses exercise-induced hypertrophy of skeletal muscle. Eur J Appl Physiol Occup Physiol. 1994;69(1):88-91.
Deschenes MR, et al. Endurance and resistance exercise induce muscle fiber type specific responses in androgen binding capacity. J Steroid Biochem Mol Biol. Aug. 1994;50(3-4):175-9.
Bamman MM, et al. Mechanical load increases muscle IGF-I and androgen receptor mRNA concentration in humans. Am J Physiol Endocrinol Metab. Mar. 2001;280(3):E383-90.
Willoughby DS, et al. Effects of sequential bouts of resistance exercise on androgen receptor expression. Med Sci Sports Exerc. Sep. 2004;36(9):1499-506.
Ratamess NA, et al. Androgen receptor content following heavy resistance exercise in men. J Steroid Biochem Mol Biol. Jan. 2005:93(1):35-42.
Kraemer WJ, et al. The effects of L-carnitine L-tartrate supplementation on hormonal responses to resistance exercise and recovery. J Strength Cond Res. Aug. 2003;17(3):455-62.
Volek JS, et al. L-carnitine L-tartrate supplementation favorably affect markers of recovery from exercise stress. Am J Physiol Endocrinol Metab. Feb. 2002;282(2):E474-82.
Giamberardino MA, et al. Effects of prolonged L-carnitine administration on delayed muscle pain and CK release after eccentric effect. Int J Sports Med. Jul. 1996;17(5):320-4.
Godard MP, et al. Body composition and hormonal adaptations associated with forskolin consumption in overweigh and obese men. Obes Res. Aug. 2005;13(8):1335-43.
Mackay D. Nutrients and botanicals for erectile dysfunction: examining the evidence. Altern Med Rev. Mar. 2004;9(1):4-16.
Giuliano F, et al. Alpha receptors in the central nervous system and its effects on erection. J Androl. 1999;20:683-7.
Guay AT, et al. Yohimbine treatment of organic erectile dysfunction in a dose-escalation trial. Int J Impot Res. Feb. 2002;14(1):25-31.
Forsling ML, et al. The effect of melatonin administration on pituitary hormone secretion in man. Clin Endocrinol (Oxf). Nov. 2002;57(5):615-20.
Vanhelder WP, et al. Growth hormone responses during intermittent weight lifting exercise in men. Eur J Appl Physiol Occup Physiol. 1984;53(1):31-4.
Goto K, et al. A single set of low intensity resistance exercise immediately following high intensity resistance exercise stimulates growth hormone secretion in men. J Sports Med Phys Fitness. Jun. 2003;43(2):243.
Meeking DR, et al. Exercise-induced GH secretion is enhanced by the oral ingestion of melatonin in healthy adult male subjects. Eur J Endocrinol. Jul. 1999;141(1):22-6.
Nassar E, et al. Effects of prophylactic N-Acetyl-5-methoxytryptamine (melatonin) supplementation and resistance exercise on serum growth hormone levels and the hypothalamus-pituitary-adrenal axis in young males and females. J Int Soc Sports Nutr 2006;3(1):S1-29 (Poster 24).
Weber C, et al. Antioxidative effect of dietary coenzyme Q10 in human blood plasma. Int J Vitam Nutr Res. 1994;64(4):311-5.
Thomas SR, et al. Inhibition of LDL oxidation by ubiquinol-10. A protective mechanism for coenzyme Q in Atherogenesis? Mol Aspects Med. 1997;18 Suppl:S85-103.

(Continued)

*Primary Examiner* — Melenie McCormick

(57) ABSTRACT

A composition comprising at least a therapeutically effective amount of L-carnitine fumarate, and an extract of *Coleus forskohlii* is provided to maintain androgen and androgen-like uptake potential in cells, via simultaneous increase in the availability of androgen receptors and improved availability of androgen and androgen-like molecules. A method of same is also provided. The present invention further comprises therapeutically effective amounts of one or more of N-acetyl L-carnitine, melatonin. ubidecarenone (coenzyme Q10), idebenone, decylubiquinone, an extract of *Agaricus blazei Murill*, and ginsenoside Rb1.

1 Claim, No Drawings

OTHER PUBLICATIONS

Kamikawa T, et al. Effects of coenzyme Q10 on exercise tolerance in chronic stable angina pectoris. Am J Cardiol. Aug. 1, 1985;56(4):247-51.

Folkers K, et al. Biochemical rationale and the cardiac response of patients with muscle disease to therapy with coenzyme Q10. Proc Natl Acad Sci USA. Jul. 1985;82(13):4513-6.

Idebenone—Monograph. Altern Med Rev. Feb. 2001;6(1):83-6.

Armstrong JS, et al. The coenzyme Q10 analog decylubiquinone inhibits the redox-activated mitochondrial permeability transition. J Biol Chem. Dec. 5, 2003;278(49):49079-84.

Liu J, et al. Protein-protein interactions mediate mitochondrial cholesterol transport and steroid biosynthesis. J Biol Chem. 2006 Dex 15;281(50):38879-93.

Chen S, et al. Anti-aromatase activity of phytochemicals in white button mushrooms (*Agaricus bisporus*). Cancer Res. Dec. 15, 2006;66(24):12026-34 (Abstract).

Tsai SC, et al. Stimulation of the secretion of luteinizing hormone by ginsenoside-Rb1 in male rats. Chin J Physiol. Mar. 2003;46(1):1-7 (Abstract).

PCT International Application No. PCT/CA2007/000835 filed May 10, 2007, International Search Report dated Feb. 12, 2008, Applicant: Multi Formulations Ltd. et al.

Saper et al., "Common Dietary Supplements for Weight Loss", American Family Physician, vol. 70-No. 9, pp. 1731-1738. (2004).

Zhang et al., "Antiangiogenic Effect of Capecitabine Combined with Ginsenoside Rg3 . . .", Cancer Biotherapy & Radiopharmaceuticals, vol. 23, No. 5, pp. 647-653 (2008).

Kraemer, W.J. et al., The Effects of L-caritine L-tartrate Supplementation on Hormonal Responses to Resistance Exercise and Recovery, Journal of Strength and Conditioning Research, 2003, 17(3):455-462, ISSN: 1064-8011.

Kraemer, W.J. et al., Androgenic Responses to Resistance Exercise: Effects of Feeding and L-Carnitine, Medicine and Science in Sports and Exercise, Jul. 2006, 38(7): 1288-1296, ISSN: 0195-9131.

Ariga, T., The antioxidative function, preventive action on disease and utilization of proanthocyanidins, Biofactors, 2004, 21(1-4): 197-201, ISSN: 0951-6433.

Brown, G.A. et al., Effects of anabolic precursors on serum testosterone concentrations and adaptations to resistance training in young men, International Journal of Sport Nutrition and Exercise Metabolism, 2000, 10 (3):340-359, ISSN: 1526-484X.

International Search Report by ISA/CA dated Aug. 27, 2008, PCT International Application No. PCT/CA2008/000880 filed May 12, 2008, Applicant: Multi Formulations Ltd et al.

\* cited by examiner

COMPOSITION FOR MAINTAINING ANDROGEN AND ANDROGEN-LIKE UPTAKE POTENTIAL BY CELLS

FIELD OF THE INVENTION

The present invention relates to a nutritional supplement for maintaining androgen and androgen-like uptake potential in cells, via simultaneous increase in the availability of androgen receptors and improved availability of androgen and androgen-like molecules. More specifically, the present invention relates to a composition comprising a synergistic combination of L-carnitine fumarate and a plant extract derived source of forskolin.

BACKGROUND OF THE INVENTION

Androgen receptors (AR) are intracellular receptors that specifically bind androgens, such as testosterone and dihydrotestosterone, but are also known to be activated by growth factors, such as insulin-like growth factor-1 (IGF-1). The influence of testosterone on skeletal muscle protein synthesis is mediated by the AR. After an androgen binds to the AR, restructuring and dimerization of the proteins occurs forming an activated receptor complex, which translocates to the nucleus and binds to DNA, thereby activating androgen-specific gene expression in the nucleus.

Animal and clinical studies indicate that the AR signaling pathway is required for the appropriate development of skeletal muscles, as it regulates increases in lean muscle mass, muscle strength, and muscle protein synthesis. The importance of AR for muscle protein accretion has been shown, since muscle hypertrophy has been shown to be attenuated by AR blockade (Inoue K, Yamasaki S, Fushiki T, Okada Y, Sugimoto E. Androgen receptor antagonist suppresses exercise-induced hypertrophy of skeletal muscle. Eur J Appl Physiol Occup Physiol. 1994;69(1):88-91).

The physiological importance of AR in exercise-induced muscle hypertrophy has been investigated in a number of human and animal studies, most of which emphasize the importance of increasing the AR content (Deschenes M R, Maresh C M, Armstrong L E, Covault J, Kraemer W J, Crivello J F. Endurance and resistance expercise induce muscle fiber type specific responses in androgen binding capacity. J Steroid Biochem Mol. Biol. 1994 August; 50(3-4):175-9), in a muscle-fiber-specific manner. For example, resistance exercise elicits significant decreases in AR content of slow oxidative skeletal muscle fibers, and a significant increase in fast glycolytic skeletal muscle fibers.

In untrained men, a single bout of heavy resistance exercise has been shown to up-regulate AR mRNA 48 hours post-training (Bamman M M, Shipp J R, Jiang J, Gower B A, Hunter G R, Goodman A, McLaffert C L Jr, Urban R J. Mechanical load increases musvle IGF-I and androgen receptor mRNA concentrations in humans. Am J Physiol Endocrinol Metab. 2001 March; 280(3):E383-90). While, repeated resistance exercise, having 48 hours between sessions, has been shown to increase AR mRNA and protein expression (Willoughby D S, Taylor L. Effects of sequential bouts of resistance exercise on androgen receptor expression. Med Sci Sports Exerc. 2004 September; 36(9):1499-506). Such augmentation has been correlated with elevated serum testosterone levels and corresponded to significant increases in myofibrillar protein.

In trained individuals, high-volume, high-intensity resistance exercise appears to cause a decrease in AR protein content within 1 hour post-exercise (Ratamess N A, Kraemer W J, Volek J S, Maresh C M, Vanheest J L, Sharman M J, Rubin M R, French D N, Vescovi J D, Silvestre R, Hatfield D L, Fleck S J, Deschenes M R. Androgen receptor content following heavy resistance exercise in men. J Steroid Biochem Mol. Biol. 2005 January:93(1):35-42), almost certainly due to protein catabolism induced by exercise-related stress. However, this negative effect is mitigated by post-resistance exercise feeding, which has been shown to increase muscle AR content, resulting in increased testosterone tissue uptake and enhanced luteinizing hormone release, via feedback mechanisms. These observations provide a possible mechanism for increased protein synthesis following post-resistance exercise food intake.

SUMMARY OF THE INVENTION

The present invention relates to a nutritional supplement for maintaining androgen and androgen-like uptake potential in cells, via simultaneous increase in the availability of androgen receptors and improved availability of androgen and androgen-like molecules. The effects of the present composition on increasing and maintaining androgens and androgen-like substances in an individual allows them to act upon an androgen receptor wherein they confer their respective endogenous effects. The nutritional supplement, comprising at least an effective amount of L-carnitine fumarate and an extract of Coleus forskohlii. In additional aspects of the present invention, one or more of N-acetyl L-carninte, melatonin, ubidecarenone (coenzyme Q10), idebenone, decylubiquinone, an extract of *Agaricus blazei Murill*, and ginsenoside Rb1 are added to the composition to provide further synergistic benefits. Both a composition and a method are provided by the present disclosure.

DETAILED DESCRIPTION OF THE INVENTION

In the following description, for the purposes of explanations, numerous specific details are set forth in order to provide a thorough understanding of the present invention. It will be apparent, however, to one of ordinary skill in the art that the present invention may be practiced without these specific details.

The present invention is directed towards a nutritional supplement, for maintaining androgens and androgen-like uptake potential in a cell, via simultaneous increase in the availability of androgen receptors and improved availability of androgen and androgen-like molecules, comprising effective sources of L-carnitine, and a plant extract providing forskolin. According to various aspects, the present invention may further comprise combinations of N-acetyl L-carnitine, melatonin, ubidecarenone (coenzyme Q10), idebenone, decylubiquinone, an extract of *Agaricus blazei Murill*, and ginsenoside Rb1.

The term 'androgen-like' as used herein is understood to represent any substance which behaves in a manner similar to that of an endogenous or exogenous androgen with respect to its actions on a cell in the body of a mammal.

The term 'uptake potential' as used herein is understood to define the ability of a cell to interact with an extracellular substance, via membrane proteins, to produce intracellular signals and protein translocation to the nucleus resulting in gene expression. It is herein understood that uptake potential is enhanced by factors including, but not limited to the increased presence of extracellular substances, increased presence of activated cell receptors as a result of reduced cell damage, enhancements of interactions between substances and receptors, and increased ability to propagate intracellular signal cascades post-receptor-substance interaction within a cell.

A used herein, the term 'nutritional composition' includes dietary supplements, diet supplements, nutritional supplements, supplemental compositions and supplemental dietary compositions or those similarly envisioned and termed compositions not belonging to the conventional definition of pharmaceutical interventions as is known in the art. Furthermore, 'nutritional compositions' as disclosed herein belong to category of compositions having at least one physiological function when administered to a mammal by conventional routes of administration.

L-Carnitine and Functional Derivatives

Carnitine, referred to as L-carnitine, is a quaternary ammonium compound synthesized from the amino acids lysine and methionine. L-carnitine plays a role in the transport of fatty acids across the mitochondrial matrix for the subsequent metabolism and energy production by beta-oxidation.

However, recent research in this area has mostly involved L-carnitine L-tartrate (LCLT), a salt of L-carnitine, and has focused on a role separate from carnitine's originally hypothesized role in fat metabolism. LCLT supplementation has been evaluated on resistance exercise trained humans as an enhancer of the hormonal responses to resistance exercise and as a recovery promoter. Three weeks of supplementation with LCLT, providing the equivalent of 2 g of elemental carnitine per day, has been shown to reduce muscle damage produced by an acute bout of high-intensity resistance exercise via cross-over, placebo controlled studies (Kraemer W J, Volek J S, French D N, Rubin M R, Sharman M J, Gomez A L, Ratamess N A, Newton R U, Jemiolo B, Craig B W, Hakkinen K. The effects of L-carnitine L-tartrate supplementation on hormonal responses to resistance exercise and recovery. J Strength Cond Res. 2003 August; 17(3):455-62). The investigators conclude that less muscle damage may have resulted in more hormonal receptors available for binding interactions with anabolic hormones. This explains the reduced progression of muscle damage, as measure by MRI, in the recovery days after resistance exercise (Volek J S, Kraemer W J, Rubin M R, Gomez A L, Ratamess N A, Gaynor P. L-carnitine L-tartrate supplementation favorably affect markers of recovery from exercise stress. Am J Physiol Endocrinol Metab. 2002 February; 282(2):E474-82).

One study has shown that 21-days of L-carnitine supplementation, with 2 g of carnitine per day, in weight-trained individuals induced significant up-regulation of pre-exercise skeletal muscle AR protein content (p<0.05) as compared to placebo (Kraemer W J, Spiering B A, Volek J S, Ratamess N A, Sharman M J, Rubin M R, French D N, Silvestre R, Hatfield D L, Van Heest J L, Vingren J L, Judelson D A, Deschenes M R, Maresh C M. Angrogenic responses to resistance exercise: effects of feeding an L-carnitine. Med Sci Sports Exerc. 2006 July; 38(7):1288-96). L-carnitine confers its function in this regard by reducing muscle damage associated with resistance exercise, therefore attenuating the catabolism of muscle-specific proteins, such as AR, for example. It is understood that L-carnitine enhances testosterone uptake via offering a protective effect resulting in a reduction in muscle damage and an increased availability of AR. It is understood the L-carnitine's effects are not conferred via direct stimulation of testosterone secretion. Based on these considerations, and on the fact that post-resistance exercise feeding stimulates increases in AR content, it is herein understood by the inventors that L-carnitine and feeding independently yet synergistically enhance the hormonal environments following resistance exercise and promote anabolism.

Furthermore, a study of the effects of L-carnitine supplementation on delayed muscle soreness (Giamberardino M A, Dragani L, Valente R, Di Lisa F, Saggini R, Vecchiet L. Effects of prolonged L-carnitine administration on delayed muscle pain and CK release after eccentric effort. Int J Sports Med. 1996 July; 17(5):320-4), showed that L-carnitine has a protective effect against pain and damage from eccentric muscular effort. This result has been attributed to the vasodilative properties of L-carnitine, which would increase the wash-out of pain inducing energy metabolites.

It is herein understood by the inventors that supplementation with the equivalent of 2 g of L-carnitine per day, will reduce the catabolism of muscle-specific proteins, resulting in enhanced testosterone uptake via the increased availability of AR. Furthermore, it is understood that the vasodilative properties of the composition will improve energetic metabolism in hypoxic muscle tissue and enhance the wash-out of pain generating energy metabolites, thus decreasing muscle damage and pain and resulting in quicker recovery following resistance exercise.

In an embodiment of the present invention, which is set forth in greater detail in the examples below, the nutritional supplement comprises effective sources of L-carnitine, such as, but not limited to, L-carnitine fumarate, L-carnitine-L-tartrate, and N-acetyl L-carnitine HCl. In addition to the aforementioned derivatives, other effective and pharmaceutically acceptable salts or ester of carnitine may be employed in the practice of the invention.

By way of example, a serving of the nutritional supplement comprises from about 0.5 g to about 5.0 g of L-carnitine fumarate, and from about 0.01 g to about 1 g of N-acetyl L-carnitine. The preferred dosage of the nutritional supplement of the present invention, comprises about 1.25 g of L-carnitine fumarate and about 0.375 g of N-acetyl L-carnitine per serving.

Coleus Forskohlii

*Plectranthus barbatus*, also known as *coleus forskohlii*, is tropical perennial plant, that is of scientific and medicinal interests since it is an abundant source of forskolin. Forskolin is a diterpene that is used to raise levels of cyclic adenosine monophosphate (cAMP) in cells, via a G-protein dependent mechanism. cAMP is a second messenger, used for intracellular signal transduction, such as transferring the effects of hormones like glucagon and adrenaline, from cell-surface receptors to the nucleus.

It is well known in the literature that lipolysis in isolated fat cells in vitro is increased by administration of forskolin. Forskolin facilitates this improved lipolysis by increasing levels of cyclic AMP (cAMP). The following other biological effects of forskolin have been described as a result of the cAMP mechanisms: increased chronotropic and inotropic effect on the heart, hypotensive action, increased synthesis of body steroids, inhibition of platelet aggregation, potentiation of insulin secretion, increased release of adrenocorticotropic hormone (ACTH), and decreased intraocular pressure.

Additionally, U.S. Pat. No. 5,804,596 discloses a method of administering forskolin to an individual in order to reduce body fat relative to lean body mass, by reducing body fat through increasing thermogenesis via increased cAMP levels. However, U.S. Pat. No. 5,804,596 does not disclose a method of increasing the availability of androgen and/or androgen-like molecules with concomitant increase in the availability of androgen receptors in skeletal muscle, thus providing for increased protein synthesis following post-resistance exercise food intake.

One study showed that, in overweight healthy male subjects, supplementation, with 250 mg of 10% forskolin extract twice a day, caused significant fat loss and lean body mass-sparing effects as compared to the placebo (Godard M P, Johnson B A, Richmond S R. Body composition and hormonal adaptations associated with forskolin consumption in overweight and obese men. Obes Res. 2005 August; 13(8): 1335-43). These effects are attributed to significant increases in free testosterone levels and a tendency towards increased endogenous total testosterone production.

Testosterone is a steroid hormone that is secreted in the testes, ovaries, and in small amounts by the adrenal glands. Production and secretion of testosterone by the Leydig cells of the testes is regulated by luteinizing hormone (LH) from the anterior pituitary. LH exerts its effects on Leydig cells through the use of a secondary messenger, cAMP. Thus, by increasing the accumulation of cAMP, by use of forskolin, it is understood to lead to an increase in testosterone production and secretion. Increased levels of testosterone will result in greater stimulation of the AR signaling pathway, leading to increases in lean muscle mass, muscle strength, and muscle protein synthesis.

In an embodiment of the present invention, which is set forth in greater detail in the examples below, the nutritional supplement comprises an extract of *Coleus forskohlii*. A serving of the nutritional supplement comprises from about 0.001 g to about 0.1 g of an extract of *Coleus forskohlii*. The preferred dosage of a serving of the nutritional supplement of the present invention comprises about 0.025 g of an extract of *Coleus forskohlii*.

Simultaneous Increase in Androgen Receptors and Androgen

While, not wishing to be bound by theory, the present invention is comprised of components for enhancing hormonal responses to resistance exercise, reduce muscle damage associated with resistance exercise and produce a protective effect against pain and damage from eccentric effort by acting as a vasodilator.

According to one embodiment of the invention, the composition comprises at least L-carnitine and Forskolin wherein the L-carintine will reduce the catabolism of muscle-specific proteins, resulting in enhanced testosterone uptake via the increased availability of AR and the use of forskolin, will lead to an increase in testosterone production and secretion. Thus the increased levels of testosterone along with the enhanced testosterone uptake will result in greater stimulation of the AR signaling pathway, leading to increases in lean muscle mass, muscle strength, and muscle protein synthesis It is herein understood by the inventors that the above combination of ingredients work synergistically to help mediate a faster recovery following resistance exercise, reduce the catabolism of muscle-specific proteins, resulting in enhanced testosterone uptake via increased availability of AR than is normally observed in the absence of such supplementation.

In additional aspects of the present invention, one or more of N-acetyl L-carninte, melatonin, ubidecarenone (coenzyme Q10), idebenone, decylubiquinone, an extract of *Agaricus blazei Murill*, and ginsenoside Rb1 are added to the composition to provide further synergistic benefits relating to maintaining androgen and androgen-like uptake potential in cells. The additional ingredients and synergistic benefits are disclosed hereinafter.

Melatonin

Melatonin, also known as Melatonine, Circadin, N-Acetyl-5-methoxytryptamine, and 5-Methoxy-N-acetyltryptamine, is naturally produced in the brain by the pineal gland and has been shown to stimulate the production of growth hormone as well as reduce free-radical damage. Evidence suggests that melatonin plays a role in modulating pituitary gland secretions such as growth hormone. Furthermore, melatonin follows a circadian rhythm and is thus principally controlled by a shift from light to dark within the environment.

Exogenous oral melatonin administration of both 0.5 mg and 5.0 mg has been shown to produce a significant increase in plasma GH concentrations with peak values at 60 minutes being similar in amplitude. Moreover, both of the aforementioned values share similar areas under the curve as detected by two site immunoradiometric assay (Forsling M L, Wheeler M J, Williams A J. The effect of melatonin administration on pituitary hormone secretion in man. Clin Endocrinol (Oxf). 1999 November; 51(5):637-42) indicating that 0.5 mg may be the maximal dose for GH stimulation. Additionally, exogenous melatonin administration was, however, shown to modulate the neurohypophysial response to different stimuli (Forsling M L, Williams A J. The effect of exogenous melatonin on stimulated neurohypophysial hormone release in man. Clin Endocrinol (Oxf). 2002 November; 57(5):615-20), which could contribute to the night-time increase in circulating concentrations of the hormones.

A release of GH has also been shown to occur in response to single bouts of both cardiovascular and resistance exercise. At 85% of the weight of the one repetition maximum for an individual, a single bout of weight lifting exercise was shown to significantly elevate the serum level of GH (Vanhelder W P, Goode R C, Radomski M W. Growth hormone responses during intermittent weight lifting exercise in men. Eur J Appl Physiol Occup Physiol. 1984;53(1):31-4.). Additionally, the serum levels of GH where shown to be increased by a single set of low- and moderate-intensity (50% and 70% of one repetition maximum respectively) resistance exercise following high intensity exercise (90% of one repetition maximum) (Goto K, Sato K, Takamatsu K. A single set of low intensity resistance exercise immediately following high intensity resistance exercise stimulates growth hormone secretion in men. J Sports Med Phys Fitness. 2003 June; 43(2):243).

Exogenous melatonin administered orally prior to bicycle exercise at 70% VO2max was shown to cause significant increases in GH when compared to placebo through a calculation of the area under the curve. In this case, 5.0 mg was administered orally 60 minutes prior to exercise and GH levels were shown to peak at 30 minutes following exercise, whereas the increase in GH levels in the placebo group peaked at 15 minutes following exercise (Meeking D R, Wallace J D, Cuneo R C, Forsling M, Russell-Jones D L. Exercise-induced GH secretion is enhanced by the oral ingestion of melatonin in healthy adult male subjects. Eur J. Endocrinol. 1999 July; 141(1):22-6). Since exercise-induced GH secretion is thought to be mediated predominantly through a hypothalamic pathway, it seems likely that melatonin facilitates GH secretion at the hypothalamic level.

Additionally, a human study has reported that, in weight-trained young males, 0.5 and 5.0 mg melatonin were significantly more effective than placebo at increasing serum free GH following a single bout of heavy-resistance exercise (Nassar E, Mulligan C, Taylor L, Kerksick C, Galbreath M, Greenwood M, Willoughby D. Effects of prophylactic N-Acetyl-5-methoxytryptamine (melatonin) supplementation and resistance exercise on serum growth hormone levels and the hypothalamus-pituitary-adrenal axis in young males and females. J Int Soc Sports Nutr 2006;3(1):S1-29 (Poster 24)). This study also investigated the effects of melatonin on IGF-1, IGFB-1 and IGFBP-3, and reported notable increases in serum IGFBP-3 during both pre- and post-exercise periods.

This suggests that melatonin may work by triggering a release of IGF-1 from IGFBP-3 in a manner different then GH-dependent release of IGF-1.

It is herein understood by the inventors that melatonin will act to increase availability of free GH, resulting in increased binding to the extracellular domain of the GH receptor thus promoting the release of the anabolic insulin-like growth factor 1 (IGF-1), which is androgen-like and interacts with AR.

In an embodiment of the present invention, which is set forth in greater detail in the examples below, the nutritional supplement comprises melatonin. A serving of the nutritional supplement comprises from about 0.00005 g to about 0.005 g of melatonin. The preferred dosage of a serving of the nutritional supplement of the present invention comprises about 0.0005 g of melatonin.

Ubidecarenone (Coenzyme Q10), Idebenone and Decylubiquinone

Coenzyme Q10 (CoQ10, ubidecarenone) is found in the mitochondria of all cells and is involved in energy production. It is found at its highest concentrations in the heart, liver, kidney and pancreas. CoQ10 is a potent antioxidant in human blood (Weber C, Sejersgard Jakobsen T, Mortensen S A, Paulsen G, Holmer G. Antioxidative effect of dietary coenzyme Q10 in human blood plasma. Int J Vitam Nutr Res. 1994;64(4):311-5) where it also acts to preserve vitamin E, another major antioxidant (Thomas S R, Neuzil J, Stocker R. Inhibition of LDL oxidation by ubiquinol-10. A protective mechanism for coenzyme Q in atherogenesis? Mol Aspects Med. 1997;18 Suppl:S85-103). As a result of CoQ10's antioxidant activity it exerts a protective effect on mitochondrial membranes, insuring the integrity of the membrane-receptor interface.

One study has shown that individuals suffering from angina were able to exercise for longer periods when receiving CoQ10 (Kamikawa T, Kobayashi A, Yamashita T, Hayashi H, Yamazaki N. Effects of coenzyme Q10 on exercise tolerance in chronic stable angina pectoris. Am J. Cardiol. 1985 Aug. 1;56(4):247-51) as compared to untreated groups. Moreover, myocardial function was improved by CoQ10 in patients with disease conditions known to involve energy production deficits (Folkers K, Wolaniuk J, Simonsen R, Morishita M, Vadhanavikit S. Biochemical rationale and the cardiac response of patients with muscle disease to therapy with coenzyme Q10. Proc Natl Acad Sci USA. 1985 July; 82(13):4513-6) wherein these patients also reported a 'subjective' improved sense of well-being.

Idebenone and decylubiquinone are synthetic CoQ10 derivatives. The former being a potent antioxidant, with the ability to fight reactive oxygen species (ROS) under low oxygen tension situations (No authors listed. Idebenone-Monograph. Altern Med Rev. 2001 February; 6(1):83-6). As a result of this inhibition of lipid peroxidation, idebenone acts to protect cell membranes, especially those of the mitochondria, from oxidative damage. Decylubiquinone has been shown to effectively block redox-dependent mitochondrial permeability transition (Armstrong J S, Whiteman M, Rose P, Jones D P. The coenzyme Q10 analog decylubiquinone inhibits the redox-activated mitochondrial permeability transition. J Biol Chem. 2003 Dec. 5; 278(49):49079-84), thereby reducing the loss of mitochondrial transmembrane potential.

It is herein understood by the inventors that compounds comprising these antioxidant quinones exert a protective effect on mitochondrial membranes (Liu J, Rone M B, Papadopoulos V. Protein-protein interactions mediate mitochondrial cholesterol transport and steroid biosynthesis. J Biol. Chem. 2006 Dec. 15; 281 (50):38879-93), thus ensuring the integrity of the membrane-receptor interface and preserving the effect of hormones on mitochondrial cholesterol transport and steroidogenesis.

In an embodiment of the present invention, which is set forth in greater detail in the examples below, the nutritional supplement comprises Ubidecarenone (Coenzyme Q10), Idebenone and Decylubiquinone. A serving of the nutritional supplement comprises from about 0.0001 g to about 0.01 g of Ubidecarenone (Coenzyme Q10), from about 0.00001 g to about 0.01 g of Idebenone, and from about 0.000001 g to about 0.0001 g of Decylubiquinone. The preferred dosage of a serving of the nutritional supplement of the present invention comprises about 0.001 g of Ubidecarenone (Coenzyme Q10), about 0.0001 g of Idebenone, and about 0.00001 g of Decylubiquinone. Optionally, the nutritional supplement of the present invention comprises about 0.0001 g of Idebenone, and about 0.00001 g of Decylubiquinone.

Agaricus Genus Mushrooms

Agaricus blazei Murill is a gilled fungus which naturally occurs in Europe and North America, and is commonly known as white and button mushroom, amongst many others. The white mushroom is a source of unsaturated fatty acid components such as linoleic, linolenic, and conjugated linoleic acids, that are utilized by the body in the biosynthesis of many compounds, for example, prostaglandins.

A study of the active components of an ethyl acetate extraction of white mushrooms, linoleic, linolenic, and conjugated linoleic acids (Chen S, Oh S R, Phung S, Hur G, Ye J J, Kwok S L, Shrode G E, Belury M, Adams L S, Williams D. Anti-aromatase activity of phytochemicals in white button mushrooms (*Agaricus bisporus*). Cancer Res, 2006 Dec. 15; 66(24):12026-34 (Abstract)), showed that these fatty acids are efficient suppressors of aromatase activity. Aromatase is an enzyme whose function is to increase the aromaticity of androgens, producing estrogens from testosterone. Aromatase activity therefore acts to decrease serum levels of testosterone, thereby inhibition of this enzyme's activitity would lead to a further increases in the levels of testosterone in the body.

*Agaricus blazei*, a mushroom providing an extract which nutritional supplement of the of present invention may also comprise has been shown to reduce blood glucose, blood pressure, cholesterol levels and the effects of arteriosclerosis.

In an embodiment of the present invention, which is set forth in greater detail in the examples below, the nutritional supplement comprises an extract of *Agaricus blazei Murill*. A serving of the nutritional supplement comprises from about 0.0001 g to about 0.01 g of an extract of *Agaricus* blazei Murill. The preferred dosage of a serving of the nutritional supplement of the present invention comprises about 0.001 g of an extract of *Agaricus* blazei Murill.

In an additional embodiment of the present invention, the nutritional supplement comprises and extract of *Agaricus blazei*. A serving of the nutritional cupplement comprises from about 0.0001 to about 0.01 of an extract of *Agaricus blazei*. The preferred dosage of a serving fo the nutritional supplement of the present invention comprises about 0.001 g of an exrtract of *Agaricus blazei*.

Ginsenoside Rb1

Ginsenosides are a class of steroid-like compounds, found exclusively in plants, *Panax quinquefoius*. Ginsenosides have been the target of research, since they are viewed as the active compounds behind the claims of ginseng's efficacy. Ginsenosides appear to affect multiple pathways, and so their effects are complex and difficult to isolate.

Ginsenoside Rb1 has been shown in animals to stimulate the secretion of lutenizing hormone (LH) after exercise (Tsai S C, et al. Stimulation of the secretion of luteinizing hormone by ginsenoside-Rb1 in male rats. Chin J. Physiol. 2003 March; 46(1): 1-7 (Abstract)). (LH) is a hormone that is synthesized and secreted by the anterior pituitary gland and is responsible for the stimulation of Leydig cell production of testosterone. It is herein understood by the inventors that increased secretion of LH will result in a greater production of testosterone, thus greater levels of serum testosterone leading to more numerous interactions of testosterone with AR. This will lead to increases in lean muscle mass, muscle strength, and muscle protein synthesis.

In an embodiment of the present invention, which is set forth in greater detail in the examples below, the nutritional supplement comprises ginsenoside Rb1. A serving of the nutritional supplement comprises 0.000001 g to about 0.0001 g of ginsenoside Rb1. The preferred dosage of a serving of the nutritional supplement comprises about 0.00005 g of ginsenoside Rb1.

In an embodiment of the present invention, which is set forth in greater detail Example 1, the nutritional supplement comprises L-carnitine fumarate, an extract of Coleus forskohlii, yohimbine HCl, N-acetyl L-carnitine, melatonin, ubidecarenone (coenzyme Q10), idebenone, decylubiquinone, an extract of *Agaricus blazei Murill*, and ginsenoside Rb1. The composition is provided in any acceptable and suitable oral dosage form as known in the art to maintain androgen and androgen-like uptake potential of cells, and minimize muscle damage associated with resistance exercise.

In another embodiment of the present invention, which is set forth in greater detail Example 2, the nutritional supplement comprises L-carnitine fumarate, idebenone, decylubiquinone, an extract of *Agaricus blazei murill*, and ginsenoside Rb1. The composition is provided in any acceptable and suitable oral dosage form as known in the art to maintain androgen and androgen-like uptake potential of cells, via simultaneous increase in the availability of androgen receptors and improved availability of androgen and androgen-like molecules, as well as to minimize muscle damage associated with resistance exercise.

Additional Embodiments for Maintaining Androgen and Androgen-Like Uptake Potential in Cells While, not wishing to be bound by theory, the present invention is comprised of components that have been shown to enhance hormonal responses to resistance exercise, reduce muscle damage associated with resistance exercise and produce a protective effect against pain and damage from eccentric effort by acting as a vasodilator. It is herein understood by the inventors that inclusion of L-Carnitine fumarate in the claimed composition will act to facilitate a faster recovery following resistance exercise, reduce the catabolism of muscle-specific proteins, resulting in enhanced testosterone uptake via increased availability of AR than is normally observed in the absence of such supplementation. Furthermore, it is understood that the vasodilative properties provided by the L-Carnitine fumarate will act to improve the energetic metabolism of the hypoxic muscle and enhance the wash-out of pain generating metabolites.

Furthermore, the present invention may additionally comprise melatonin which has been shown to increase serum free GH after heavy-resistance exercise, and induce a trend towards elevated levels of IGFBP-3. It is herein understood by the inventors that the increased availability of GH will increase binding to the extracellular domain of the GH receptor and promote the release of the anabolic insulin-like growth factor 1 (IGF-1), which is androgen-like and is known to interact with AR.

Additionally, the present invention comprises an extract of *Coleus forskolhii* which has been shown to have a favorable effect on enhancing serum testosterone levels, via cAMP-mediated LH effects on endogenous testosterone production as well as increasing secretion of LH. It is herein understood by the inventors that increased testosterone will result in greater stimulation of the AR signaling pathway, leading to increases in lean muscle mass, muscle strength, and muscle protein synthesis.

In addition, the present invention may additionally comprise Ubidecarenone (Coenzyme Q10) and/or derivatives thereof, which exhibit antioxidant activities and have protective effects on mitochondrial membranes (Liu J, Rone M B, Papadopoulos V. Protein-protein interactions mediate mitochondrial cholesterol transport and steroid biosynthesis. J Biol. Chem. 2006 Dec. 15; 281(50):38879-93). It is herein understood by the inventors that these protective effects will ensure the integrity of the membrane-receptor interface and preserve the effect of hormones on mitochondrial cholesterol transport and steroidogenesis.

Further to the aforementioned functions, the present invention may additionally comprise components, for example *Agaricus* blazei, which acts to suppress aromatase activity and estrogen biosynthesis (Chen S, Oh S R, Phung S, Hur G, Ye J J, Kwok S L, Shrode G E, Belury M, Adams L S, Williams D. Anti-aromatase activity of phytochemicals in white button mushrooms (*Agaricus bisporus*). Cancer Res, 2006 Dec. 15; 66(24):12026-34 (Abstract)). It is herein understood by the inventors that suppression of the activity of aromatase will result in increased serum testosterone levels, yielding greater stimulation of the AR signaling pathway, leading to increases in lean muscle mass, muscle strength, and muscle protein synthesis.

According to various embodiments of the present invention, the nutritional supplement may be consumed in any form. For instance, the dosage form of the nutritional supplement may be provided as, e.g., a powder beverage mix, a liquid beverage, a ready-to-eat bar or drink product, a capsule, a liquid capsule, a tablet, a caplet, or as a dietary gel. The preferred dosage forms of the present invention are as a caplet or as a liquid capsule.

Furthermore, the dosage form of the nutritional supplement may be provided in accordance with customary processing techniques for herbal and nutritional supplements in any of the forms mentioned above. Additionally, the nutritional supplement set forth in the example embodiments herein disclosed may contain any appropriate number and type of excipients or additional ingredients, as is well known in the art.

By way of ingestion of the composition of the present invention, a method for substantially simultaneously reducing the catabolism of muscle-specific proteins as well as stimulating the production of and inhibition of the degradation of androgen and androgen-like substances is provided. The increase of androgen and androgen-like substances resulting from the method of the present invention then confer their respective actions on androgen receptors. The method of the present invention comprises at least the step of administering to an individual a therapeutically acceptable amount of the composition of the present invention.

Although the following examples illustrate the practice of the present invention in two of its embodiments, the examples should not be construed as limiting the scope of the invention.

Other embodiments will be apparent to one of skill in the art from consideration of the specifications and example.

EXAMPLES

Example 1

A nutritional supplement comprising the following ingredients per serving is prepared for consumption as a caplet to be consumed twice daily:

About 1.25 g of L-carnitine fumarate and about 0.025 g of an extract of *Coleus forskohlii* standardized to 10% forskolin.

Preferably, the nutritional supplement is consumed in accordance with the following directions:

Directions: The supplement should be consumed in 2 servings per day, one taken with a main meal and the other with a pre-workout meal (generally consumed 1 hr prior to commencement of exercise). On non-workout days, the supplement should be taken with main meals, one of which is dinner. Supplementation should last for a 21 day cycle, with a 7 to 10 day wash-out period before commencement of another treatment round.

Example 2

A nutritional supplement comprising the following ingredients per serving is prepared for consumption as a caplet to be consumed twice daily:

About 1.25 g of L-carnitine fumarate, about 0.025 g of an extract of *Coleus forskohlii* standardized to 10% forskolin, about 0.375 g of N-acetyl L-carnitine, about 0.0005 g of melatonin, about 0.001 g of ubidecarenone (coenzyme Q10), about 0.001 g of Idebenone, about 0.00001 g of dexylubiquinone, about 0.001 g of an extract of *Agaricus blazei Murill*, and about 0.00005 g of ginsenoside Rb1.

Preferably, the nutritional supplement is consumed in accordance with the following directions:

Directions: The supplement should be consumed in 2 servings per day, one taken with a main meal and the other with a pre-workout meal (generally consumed 1 hr prior to commencement of exercise). On non-workout days, the supplement should be taken with main meals, one of which is dinner. Supplementation should last for a 21 day cycle, with a 7 to 10 day wash-out period before commencement of another treatment round.

Example 3

A nutritional supplement comprising the following ingredients per serving is prepared for consumption as a caplet to be consumed twice daily:

About 1.125 g of L-carnitine fumarate, about 0.0001 g og idebenone, about 0.00001 g of decylubiquinone, about 0.001 g of an extract of *Agaricus blazei murill*, and about 0.00005 g of ginsenoside Rb1.

Preferably, the nutritional supplement is consumed in accordance with the following directions:

Directions: The supplement should be consumed in 2 servings per day, one taken with a main meal and the other with a pre-workout meal (generally consumed 1 hr prior to commencement of exercise). On non-workout days, the supplement should be taken with main meals, one of which is dinner. Supplementation should last for a 21 day cycle, with a 7 to 10 day wash-out period before commencement of another treatment round.

EXTENSIONS AND ALTERNATIVES

In the foregoing specification, the invention has been described with specific embodiments thereof; however, it will be evident that various modifications and changes may be made thereto without departing from the broader spirit and scope of the invention.

What is claimed:

1. A composition for maintaining androgen and androgen-like substance uptake potential in cells, wherein said composition consists essentially of about 1.25 g of L-carnitine fumarate, about 0.025 g of an extract of *Coleus forskohlii* standardized to 10% forskolin, about 0.375 g of N-acetyl L-carnitine, about 0.0005 g of melatonin, about 0.001 g of ubidecarenone (coenzyme Q10), about 0.001 g of idebenone, about 0.00001 g of decylubiquinone, about 0.001 g of an extract of *Agaricus blazei Murill*, and about 0.00005 g of ginsenoside Rb1.

* * * * *